US008551311B2

(12) United States Patent
Woodward et al.

(10) Patent No.: US 8,551,311 B2
(45) Date of Patent: Oct. 8, 2013

(54) IONIC PROBE

(75) Inventors: John Robert Woodward, Windsor, CO (US); Pierre Antoine Robert Livrozet, Caluire et Cuire (FR); Jean-Francois Maurice Rene Schvan, Genay (FR); Russell Martin Young, Fort Collins, CO (US); Kevin James West, Loveland, CO (US)

(73) Assignee: Hach Company, Loveland, CO (US)

( * ) Notice: Subject to any disclaimer, the term of this patent is extended or adjusted under 35 U.S.C. 154(b) by 1329 days.

(21) Appl. No.: 12/249,727

(22) Filed: Oct. 10, 2008

(65) Prior Publication Data

US 2009/0101524 A1    Apr. 23, 2009

Related U.S. Application Data

(63) Continuation-in-part of application No. 11/516,186, filed on Sep. 6, 2006, now Pat. No. 8,366,895.

(60) Provisional application No. 60/982,495, filed on Oct. 25, 2007.

(51) Int. Cl.
    *G01N 27/26*    (2006.01)
(52) U.S. Cl.
    USPC .................. 204/433; 204/435; 204/400
(58) Field of Classification Search
    USPC ............... 204/416–420, 433, 435; 324/438
    See application file for complete search history.

(56) References Cited

U.S. PATENT DOCUMENTS

| | | | |
|---|---|---|---|
| 4,196,383 A | 4/1980 | Teass, Jr. | |
| 4,440,619 A | 4/1984 | Daroczy et al. | |
| 4,650,562 A | 3/1987 | Harman, III et al. | |
| 4,686,011 A | 8/1987 | Heiner | |
| 5,158,083 A | 10/1992 | Sacristan et al. | |
| 5,198,093 A * | 3/1993 | Sydlowski et al. | 204/406 |
| 5,405,510 A * | 4/1995 | Betts et al. | 205/782 |
| 5,789,250 A | 8/1998 | Ikezaki | |
| 6,106,692 A | 8/2000 | Kunimatsu et al. | |
| 6,395,158 B1 | 5/2002 | King et al. | |
| 6,447,670 B1 * | 9/2002 | Holmstrom | 205/775 |
| 6,551,478 B1 | 4/2003 | Bielawski et al. | |
| 7,182,847 B1 | 2/2007 | Millar et al. | |

(Continued)

FOREIGN PATENT DOCUMENTS

| DE | 10160213 A1 | 6/2003 |
|---|---|---|
| DE | 10351682 A1 | 7/2004 |

(Continued)

OTHER PUBLICATIONS

U.S. Appl. No. 11/516,186, filed Sep. 2007, Woodward et al.*

(Continued)

*Primary Examiner* — Keith Hendricks
*Assistant Examiner* — Bach Dinh
(74) *Attorney, Agent, or Firm* — Ference & Associates LLC

(57) ABSTRACT

An ionic probe is provided according to the invention. The ionic probe includes an active electrode configured to generate a measurement signal for an external test fluid, a first reference electrode configured to generate a first reference signal, and an at least second reference electrode configured to generate at least a second reference signal. The measurement signal is compared to the first reference signal and the at least second reference signal in order to determine an ionic measurement of the external test fluid.

26 Claims, 13 Drawing Sheets

(56) References Cited

U.S. PATENT DOCUMENTS

| | | | |
|---|---|---|---|
| 7,189,314 B1* | 3/2007 | Pace et al. | 204/412 |
| 2007/0215466 A1 | 9/2007 | Okada et al. | |
| 2008/0053825 A1* | 3/2008 | Woodward et al. | 204/416 |

FOREIGN PATENT DOCUMENTS

| | | |
|---|---|---|
| EP | 0156376 A | 10/1985 |
| EP | 1219959 A | 7/2002 |
| JP | S62-043557 A1 | 2/1987 |
| JP | 2005501252 A1 | 1/2005 |
| WO | WO-03/019165 A | 3/2003 |
| WO | 2007109560 A1 | 9/2007 |

OTHER PUBLICATIONS

U.S. Appl. No. 11/259,932, filed Mar. 2006, Mansouri et al.*

* cited by examiner

SECTION AA

SECTION AA

IONIC PROBE

RELATED APPLICATIONS

This application is a continuation-in-part of U.S. patent application Ser. No. 11/516,186, filed on Sep. 6, 2006, and entitled "Differential pH probe," and claims a common filing date for material in common with this application. Further, this application claims benefit of, and priority from, U.S. provisional patent application No. 60/982,495, filed on Oct. 25, 2007, and entitled "Ionic Probe". The provisional is herein incorporated by reference.

BACKGROUND OF THE INVENTION

1. Field of the Invention

The invention is related to the field of an ionic probe.

2. Statement of the Problem

A measure of the ionic level of a fluid is desirable in many situations, including testing of fluids in manufacturing settings, for pharmaceutical production, food processing and/or food quality, water quality testing, etc. Measurement of an ionic level or activity can indicate completion of a reaction, indicate fractions of components, etc.

One measure can comprise a measure of a pH level, which comprises a measure of acidity of the fluid being tested. The pH measurement can indicate the acidic or basic condition or level of the fluid.

A pH measurement comprises a measurement of hydrogen ions in a solution, expressed as a logarithmic number between about zero and fourteen (sometimes extending into negative numbers for exceedingly acidic solutions). On the pH scale, a very acidic solution has a low pH value, such as zero or one, corresponding to a large concentration of hydrogen ions ($H^+$). In contrast, a very basic solution has a high pH value, corresponding to a very small number of hydrogen ions (or to a correspondingly large number of $OH^-$ ions). A neutral solution, such as substantially pure water, has a pH value of about seven.

A pH measurement probe typically includes an active electrode unit and a reference electrode unit. The active electrode unit comprises a glass tube with an ion sensitive glass bulb at one end. The tube contains an electrolyte and an active electrode. The reference electrode unit can likewise comprise a glass tube with an ion sensitive glass bulb at one end, an electrolyte, and a reference electrode.

For each of the electrode units, the hydrated layer of glass on the exterior of the ion sensitive bulb exchanges hydrogen ions with the fluid to be tested. This produces a charge in the hydrated layer on the outside of the bulb. The internal electrolyte interacts with the ion sensitive glass and reflects a voltage potential developed in the hydrated layer of the glass due to the constant ion concentration of the electrolyte inside the glass envelope. Therefore, the voltage potential across the glass membrane is the result of the difference between the inner and outer electrical charges.

The reference buffer solution is in ionic communication with the external fluid being tested. A potential difference (i.e., voltage) between the active and reference glass electrodes is thereby formed, similar to a battery. The voltage potential between the electrodes is directly related to the ion concentration of the solution. The reference electrode provides a stable potential against which the measuring electrode can be compared. The voltage potential can be processed according to a table, formula, or other algorithm to arrive at an ionic concentration measurement, such as a pH value, for example.

The accuracy of ionic and/or pH measurements can be affected by various factors, including temperature and/or improper or contaminated electrolyte solutions, for example. A common source of inaccuracy can be an improper or inaccurate reference signal generated from a reference electrode. If the reference signal is inaccurate, the resulting pH or ion measurement will be affected. Consequently, it is of great importance that a proper and accurate reference value be obtained.

SUMMARY OF THE INVENTION

An ionic probe is provided according to the invention. The ionic probe comprises an active electrode configured to generate a measurement signal for an external test fluid, a first reference electrode configured to generate a first reference signal, and an at least second reference electrode configured to generate at least a second reference signal. The measurement signal is compared to the first reference signal and the at least second reference signal in order to determine an ionic measurement of the external test fluid.

An ionic probe is provided according to the invention. The ionic probe comprises an inner shell forming an active chamber and including an active electrolyte solution and an active ion sensitive region that protrudes from the probe and is adapted to contact an external test fluid, with the active ion sensitive region allowing ion interaction between the active electrolyte solution and the external test fluid, and an active electrode located in the active chamber and configured to generate a measurement signal related to an ionic potential between the external test fluid and the active electrolyte solution. The ionic probe further comprises a middle divider located inside the inner shell and forming a first reference chamber, with the first reference chamber holding a first reference solution and including at least one first ion sensitive region formed in the inner shell, with the at least one first ion sensitive region allowing ion interaction between the first reference solution and a middle solution that is external to the inner shell at the first ion sensitive region, and a first reference electrode located within the first reference chamber and configured to generate a first reference signal related to an ionic potential between the first reference solution and the middle solution. The ionic probe further comprises a middle shell forming a second reference chamber and holding a second reference solution and including at least one second ion sensitive region formed in the middle shell, with the at least one second ion sensitive region allowing ion interaction between the second reference solution and an outer solution that is external to the middle shell at the second ion sensitive region, and a second reference electrode located in the second reference chamber and configured to generate at least a second reference signal related to an ionic potential between the second reference solution and the outer solution. The measurement signal is compared to the first reference signal and the at least second reference signal in order to determine an ionic measurement of the external test fluid.

An ionic meter is provided according to the invention. The ionic meter comprises an ionic probe comprising an active electrode configured to generate a measurement signal for an external test fluid, a first reference electrode configured to generate a first reference signal, and at least a second reference electrode configured to generate an at least second reference signal. The ionic meter further comprises a cable coupled to the ionic probe and meter electronics coupled to the cable and configured to receive the measurement signal, the first reference signal, and the at least second reference signal. The meter electronics is further configured to compare the measurement signal to the first reference signal and the at least second reference signal in order to determine an ionic measurement of the external test fluid.

A self-correction method for an ionic meter is provided according to the invention. The method comprises generating a measurement signal, generating a first reference signal, generating at least a second reference signal, and comparing the measurement signal to the first reference signal and the at least second reference signal in order to determine an ionic measurement of an external test fluid.

DESCRIPTION OF THE DRAWINGS

The same reference number represents the same element on all drawings. It should be understood that the drawings are not necessarily to scale.

DETAILED DESCRIPTION OF THE INVENTION

FIGS. 1-13 and the following description depict specific examples to teach those skilled in the art how to make and use the best mode of the invention. For the purpose of teaching inventive principles, some conventional aspects have been simplified or omitted. Those skilled in the art will appreciate variations from these examples that fall within the scope of the invention. Those skilled in the art will appreciate that the features described below can be combined in various ways to form multiple variations of the invention. As a result, the invention is not limited to the specific examples described below, but only by the claims and their equivalents.

Figure 1:
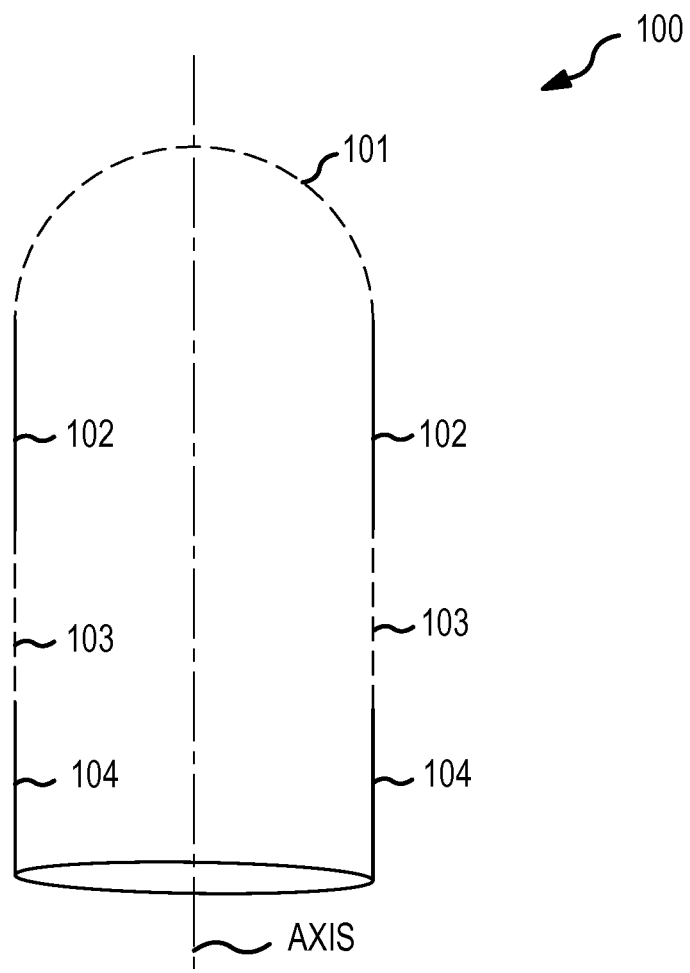
FIG. 1 illustrates glass piece used in differential pH probe, in an example embodiment of the invention.

FIG. 1 illustrates glass piece 100 used in differential pH probe 150 (shown in FIG. 4), in an example embodiment of the invention. Glass piece 100 is depicted as a tube, although other suitable shapes could be used. A generalized cylinder is a cylinder where the cross section can be any shape. Glass piece 100 includes active areas 101 and 103, in addition to non-active areas 102 and 104. Active areas 101 and 103 are formed of pH sensitive glass. An example of pH-sensitive glass is lithium-ion conductive glass. Non-active areas 102 and 104 are formed by non-pH sensitive glass. Note that alternative materials other than glass could be used for piece 100, such as pH-sensitive polymers and plastics.

Note that both the active and non-active areas are integrated together to form a single piece of glass—glass piece 100. This integration could be accomplished by treating a single glass tube to form the active and non-active areas. Alternatively, the active and non-active areas could be formed separately from one another and then fused together to form glass piece 100.

Note that active areas 101 and 103 share the same axis, making them co-axial with one another. The co-axial configuration allows for a large active area 101 while reducing the overall size of the probe 150. The single piece configuration provides structural strength and requires fewer seals than a multiple piece configuration.

Figure 2:
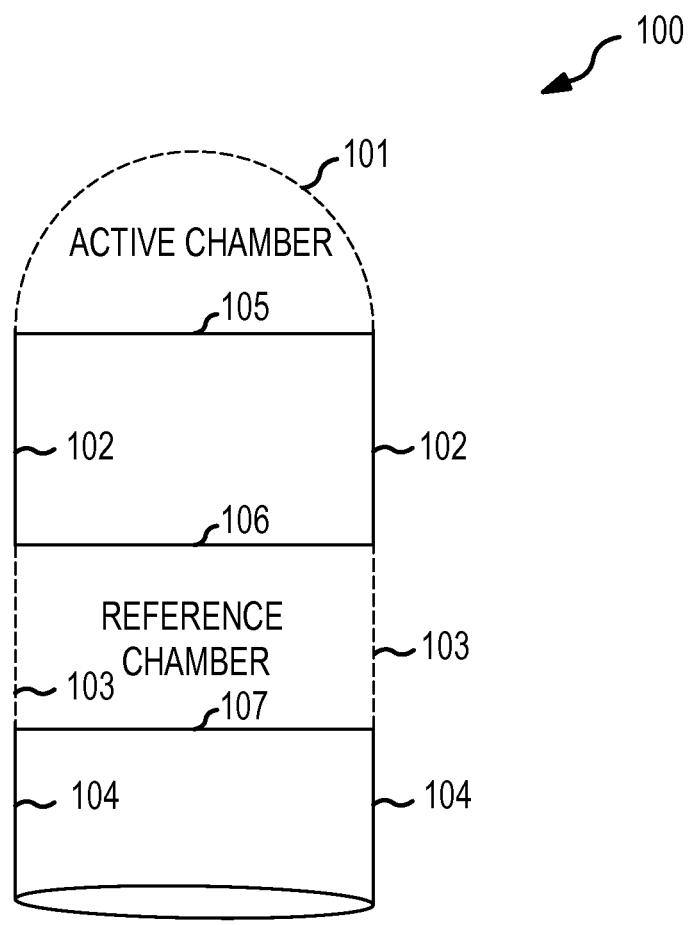
FIG. 2 illustrates glass piece with seals, in an example embodiment of the invention.

FIG. 2 illustrates glass piece 100 from FIG. 1, in an example embodiment of the invention. Glass piece 100 now has seals 105, 106, and 107. Seals 105-107 could be rubber, silicon, or some other suitable insulating material. Active area 101 and seal 105 form a first chamber, referred to as the active chamber. Active area 103 and seals 106-107 form a second chamber, referred to as the reference chamber. Both the active and reference chambers are filled with an electrolyte solution. In one example embodiment of the invention, glass piece 100 may be called a container that is divided into a number of different chambers.

Figure 3:
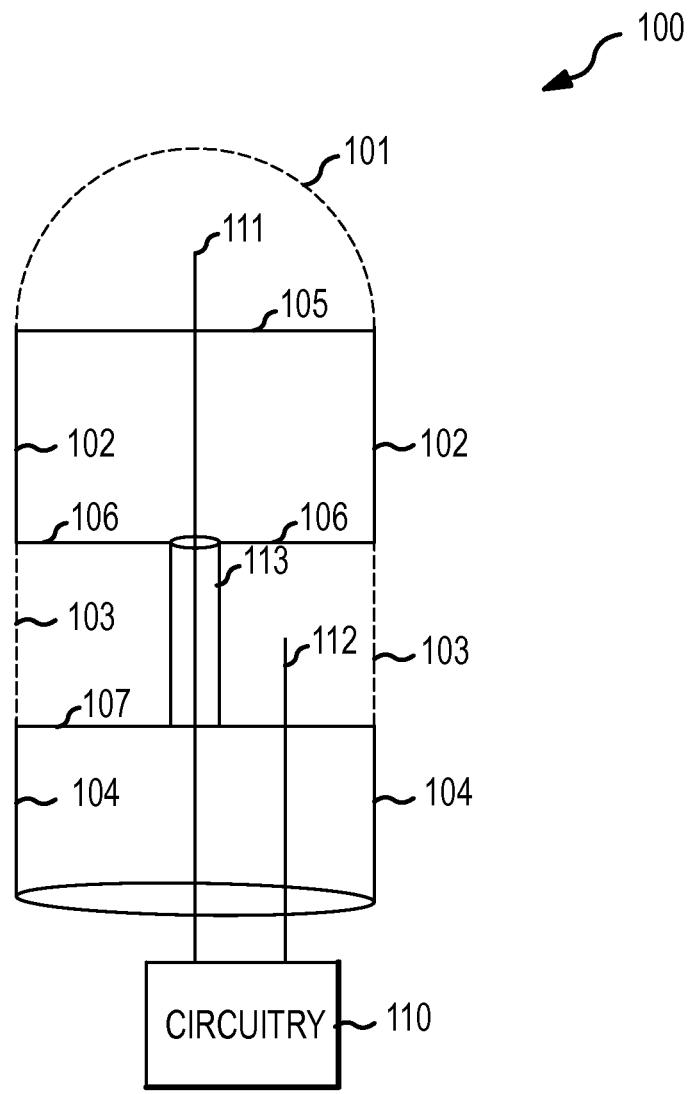
FIG. 3 illustrates glass piece with seals and circuitry, in an example embodiment of the invention.

FIG. 3 illustrates glass piece 100 from FIG. 2 and also shows circuitry 110. Glass piece 100 includes active electrode 111 that is exposed within the active chamber and then runs to circuitry 110. Note that insulating tube 113 is used so that active electrode 111 runs through the center of the reference chamber, but is not exposed within the reference chamber. Glass piece 100 also includes reference electrode 112 that is exposed within the reference chamber and then runs to circuitry 110.

Figure 4:
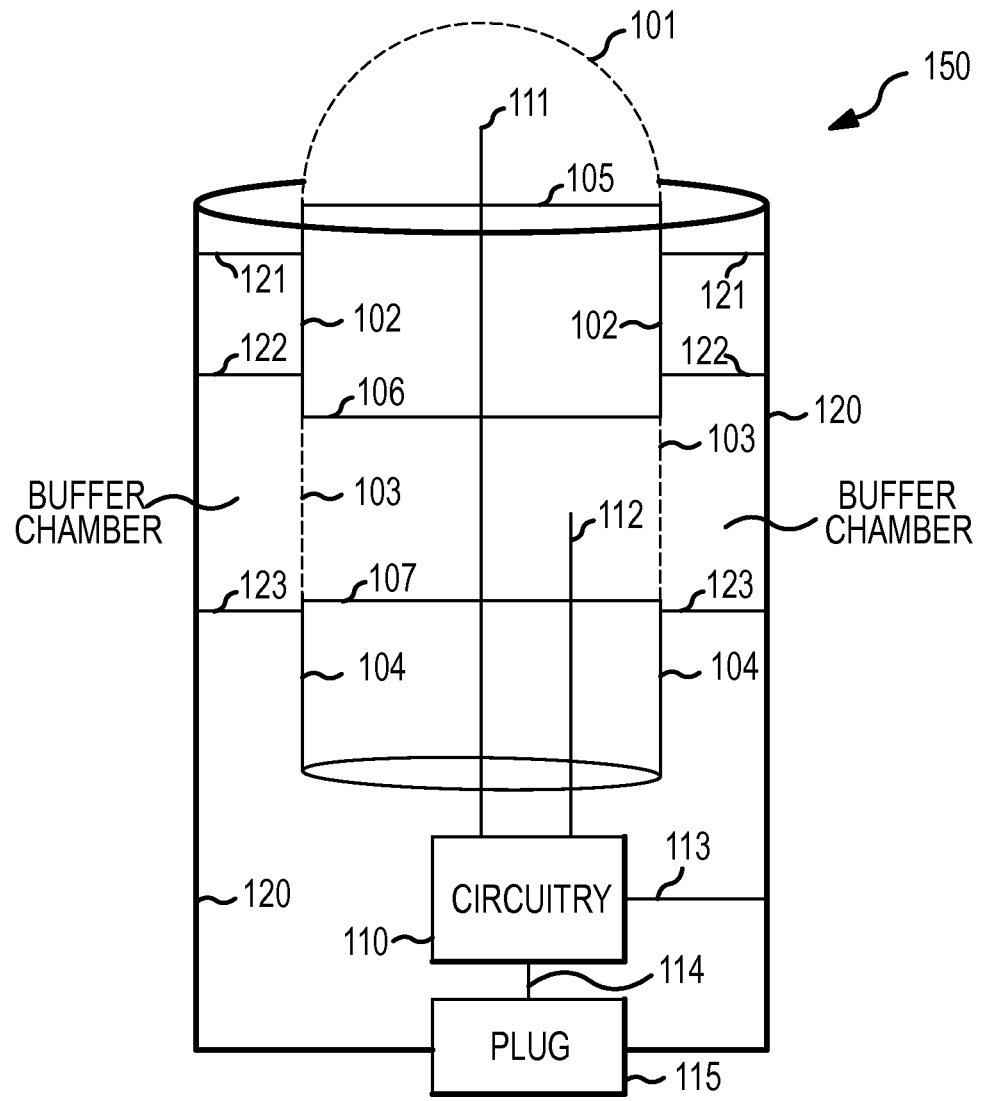
FIG. 4 illustrates differential pH probe, in an example embodiment of the invention.

FIG. 4 illustrates differential pH probe 150 in an example of the invention. Probe 150 includes glass piece 100 and circuitry 110 as described in FIGS. 1-3. Probe 150 also includes conductive enclosure 120. Conductive enclosure 120 could be tube-shaped like glass piece 100, although other shapes could be used. Glass piece 100 and circuitry 110 are placed within conductive enclosure 120.

Conductive enclosure 120 includes seals 121, 122, and 123. In this example with glass piece 100 and enclosure 120 being tube-shaped, seals 121-123 could be doughnut-shaped discs, although other shapes could be used in other examples. These disks could have much larger contact areas than conventional o-rings in order to provide better seals. Seals 121-123 could be rubber, silicon, or some other insulating material. Seals 121-122 provide a junction that allows electrical conductivity, but not fluid transfer, between the buffer chamber and the sample being tested. To provide this junction, seals 121-122 could be silicon disks with ceramic frits (tubes), where seals 121-122 are separated by a salt gel to form a salt bridge.

Seal 121 seals the end of enclosure 120 so that active area 101 of the active chamber may remain exposed to an external sample, but so that the external sample will not enter the enclosure 120. Enclosure 120, seals 122-123, and active area 103 form a buffer chamber around active area 103 of glass piece 100. This buffer chamber is filled with a buffer solution that maintains a constant pH—typically about seven.

Circuitry 110 is grounded to conductive enclosure 120 by electrical line 113. Circuitry 110 is coupled to plug 115 by electrical lines 114. Thus, circuitry 110 communicates with external systems through lines 114 and plug 115. In other embodiments, circuitry 110 may communicate with an external system using a wireless or non-contact technology, for example an optical link or an RF link.

In operation, active area 101 of probe 150 is dipped into the sample whose pH will be determined. Note that seal 121 prevents the sample from entering the enclosure 120. The sample (with unknown pH) interacts with active area 101 to produce a first voltage across active area 101. This first voltage is referred to as the active voltage and corresponds to the unknown pH of the sample. Active electrode 111 detects the active voltage and indicates the active voltage to circuitry 110.

In a similar manner, the buffer solution (with known pH) interacts with active area 103 to produce a second voltage across active area 103. This second voltage is referred to as the reference voltage and corresponds to the known pH of the buffer solution. Reference electrode 112 detects the reference voltage and indicates the reference voltage to circuitry 110.

Circuitry 110 processes the active and reference voltages in the conventional manner to determine the pH of the sample. Circuitry 110 indicates the pH of the sample to external systems (not shown) that are plugged into plug 115.

Conductive enclosure 120 is typically held by hand during testing. Note that conductive enclosure 120 electrically shields the internal components of probe 150 (i.e., the electrodes 111-112 and the circuitry 110) from hand capacitance. Conductive enclosure 120 also provides a ground. Note that conductive enclosure 120 could be stainless steel, aluminum, or some other conductive material. In one example embodiment of the invention, conductive enclosure 120 may have a conducting part and a non-conducting part. The conductive part would begin just below the seal 123 and would cover and shield the lower portion of the probe 150, including the circuitry 110. The upper portion starting just below the seal 123 would be made from a non-conductive material or have a non-conductive coating. When using the two part enclosure, a separate ground rod may be located in the outer salt bridge seal 121.

Figure 5:
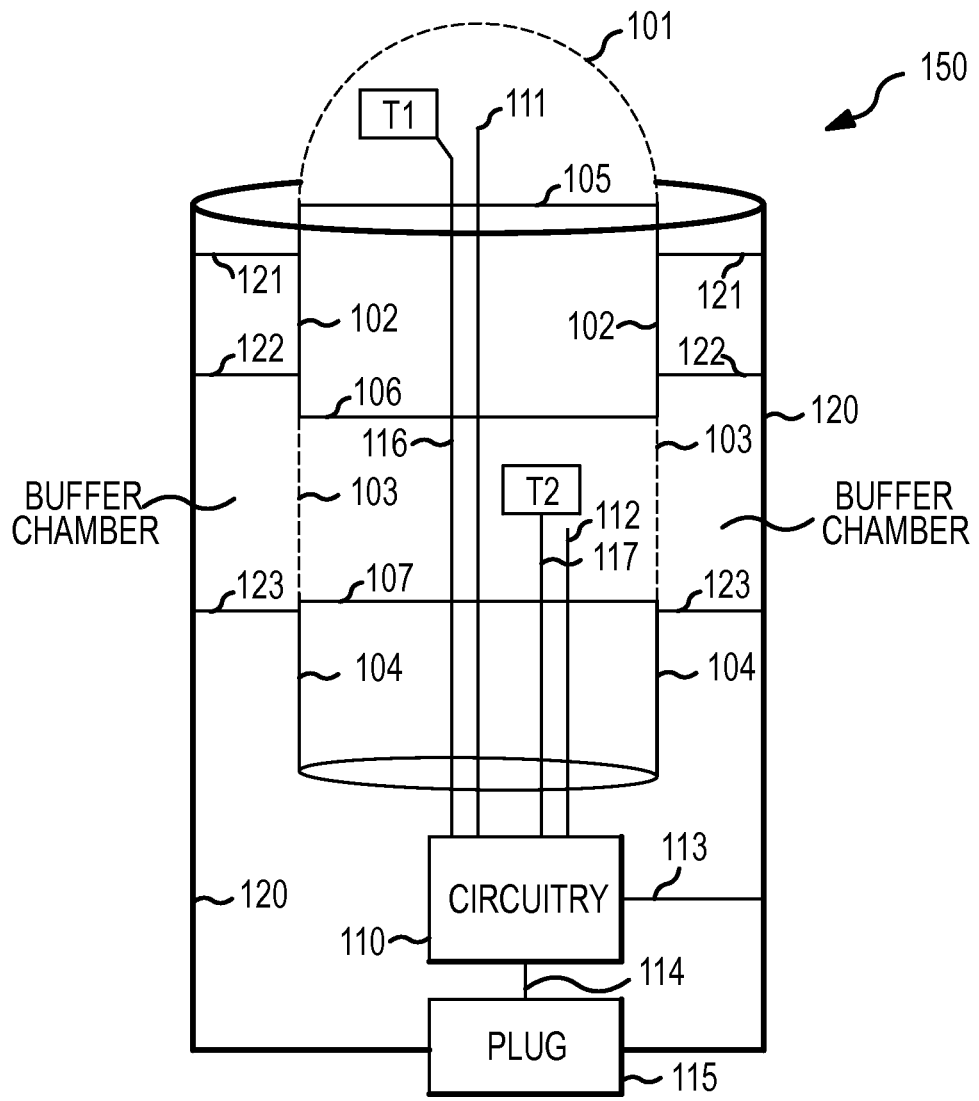
FIG. 5 illustrates differential pH probe with temperature sensors, in an example embodiment of the invention.

FIG. 5 illustrates differential pH probe 150 in an example of the invention. Thermistor T1 has been added to the active chamber to detect the temperature near the active electrode 111. Thermistor T2 has been added to the reference chamber to detect the temperature near the reference electrode 112. Thermistors T1 and T2 could be integrated within seals 105-107. Thermistor T1 transfers its temperature information to circuitry 110 over electrical line 116. Thermistor T2 transfers its temperature information to circuitry 110 over electrical line 117. Circuitry processes the temperature information from the thermistors T1 and T2 to provide temperature compensation during the pH determination. In another embodiment of the invention, the thermistor T1 may be located on the outside of the active chamber (not shown) and be exposed to the sample and used to detect the temperature of the sample. In another embodiment of the invention, the thermistor T2 may be located in the buffer chamber.

Figure 6:
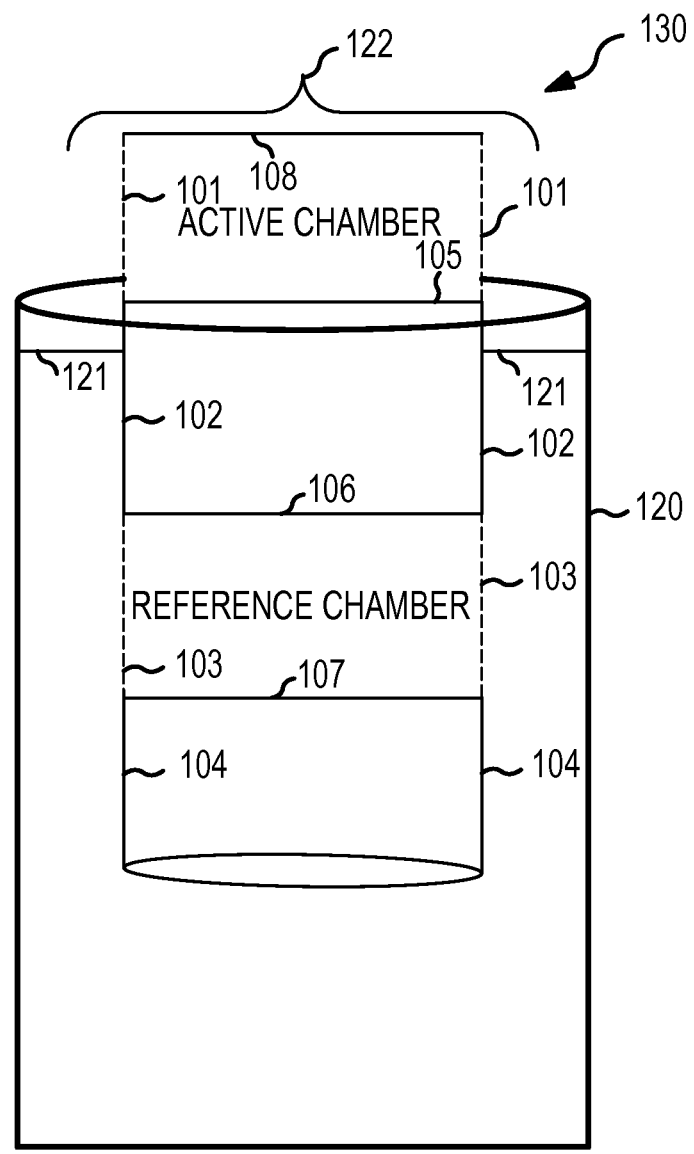
FIG. 6 illustrates glass piece used in a differential pH probe in an example embodiment of the invention.

FIG. 6 illustrates an alternative to glass piece 100. Note that some details from the previous figures are omitted for clarity. Glass piece 130 is now used for probe 150 instead of glass piece 100. Glass piece 130 is similar to the glass piece 100 with active areas 101 and 103 and non-active areas 102 and 104 separated by seals 105-107 to form the active and reference chambers. The variation from the glass piece 100 is in the shape of the active chamber. Active area 101 is no longer a dome at the top of the glass piece, but is now formed by the walls of glass piece 130 in the same way that active area 103 forms the reference chamber. Thus, the active chamber has the same geometry as the reference chamber. Non-active glass 108 is used at the top of the active chamber, although a seal could be used instead of non-active glass 108 if desired. The top of the active chamber is protected by cap 122. Cap 122 could be rubber, metal, or some other protective material that is adhered to glass piece 130.

Figure 7:
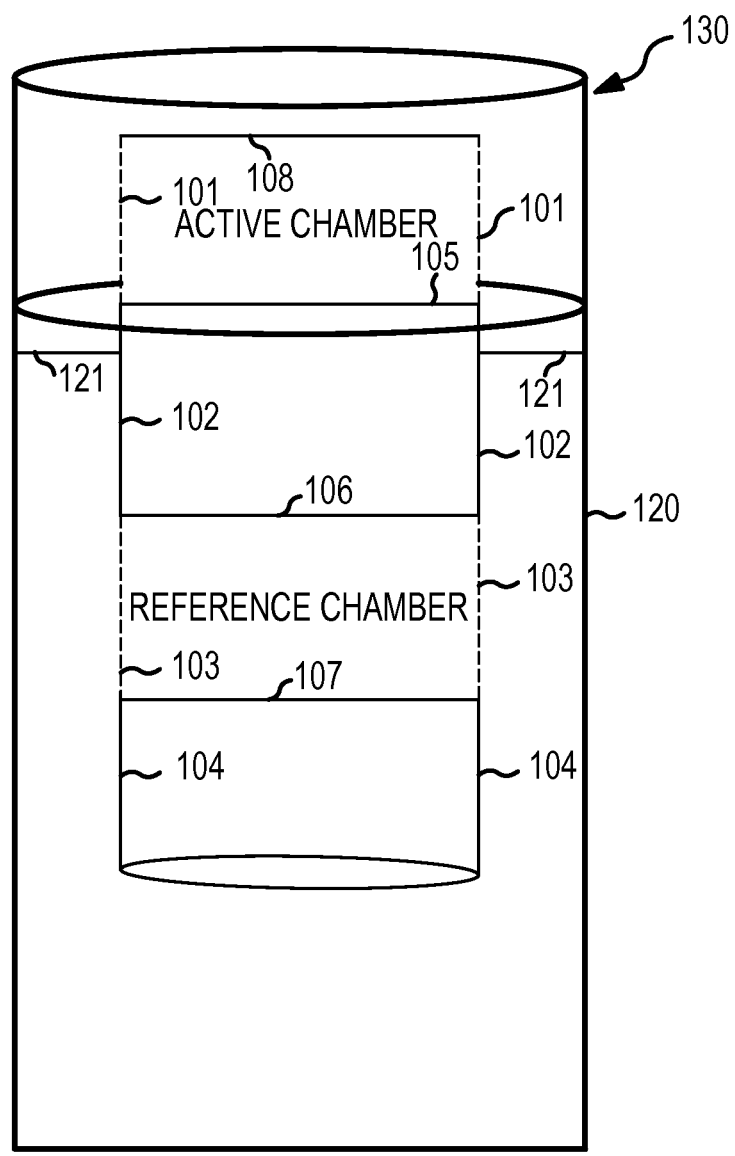
FIG. 7 illustrates a variation for conductive enclosure in another example embodiment of the invention.

FIG. 7 illustrates a variation for conductive enclosure 120. Note that some details from the previous figures are omitted for clarity. Glass piece 130 is used, but glass piece 100 could be used as well. Enclosure 120 now extends above the active chamber of glass piece 130 to provide protection. The extension of enclosure 120 must still allow the sample to contact the active area 101, so openings in the enclosure 120 should be provided for this purpose. The sample should still not be allowed to pass the seal 121.

Figure 8:
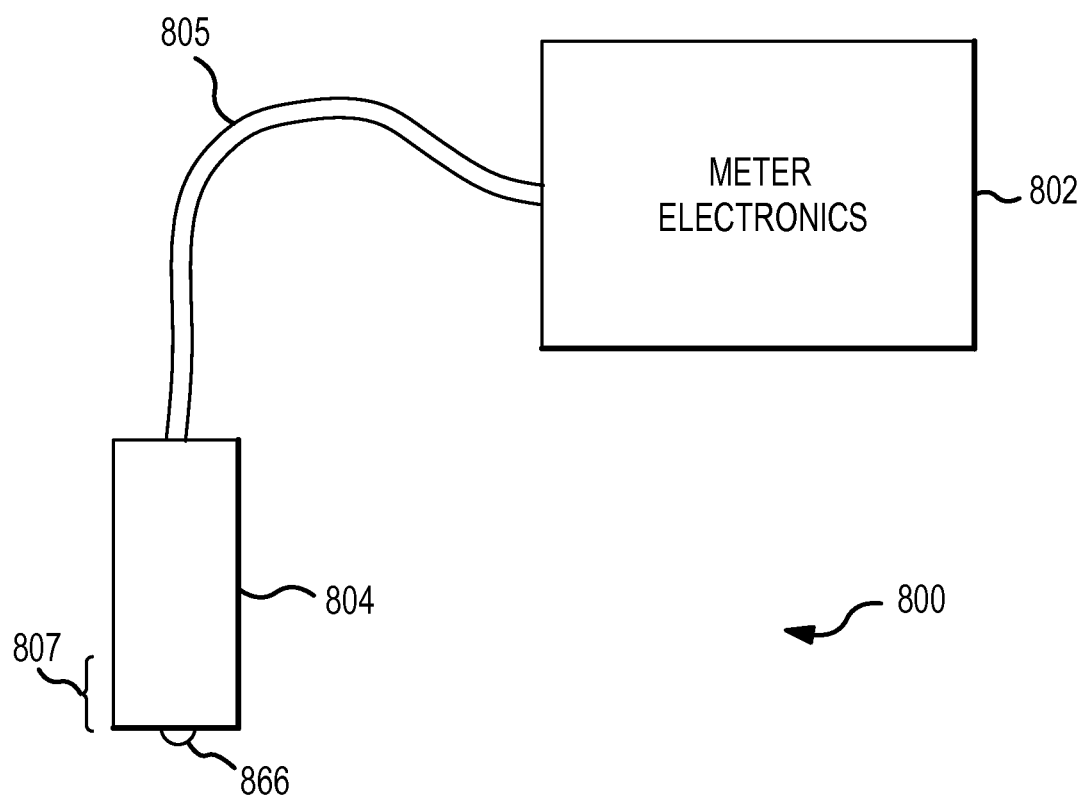
FIG. 8 shows an ion meter according to an embodiment of the invention.

FIG. 8 shows an ion meter 800 according to an embodiment of the invention. The ion meter 800 includes an ionic probe 804, a meter electronics 802, and a cable 805 connecting the ionic probe 804 to the meter electronics 802. The ionic probe 804 can include a test end 807.

In use, the ionic probe 804 is placed in an external test fluid. The test end 807 is contacted to or immersed in the external test fluid, although the entire ionic probe 804 can be immersed. The external test fluid can comprise water, for example, although it should be understood that various other fluids can be tested. To that end, the ionic probe 804 includes an active ion sensitive region 866 that is immersed in and interacts with the sample fluid. In some embodiments, the active ion sensitive region 866 comprises an active pH sensitive region 866.

The ionic probe 804 generates a voltage signal that is transferred to the meter electronics 802 by the cable 805. The voltage signal generated by the ionic probe 804 is related to an ion level or ion concentration within the external test fluid.

The meter electronics 802 receives the voltage signal from the ionic probe 804 and processes the signal in order to obtain an ionic measurement, such as a pH value, for example. The processing can include comparing the voltage signal to at least one reference signal, wherein the ionic measurement can be determined from a variation between the voltage signal and the reference signal. Therefore, it is important that the reference signal be steady and continuous in order to serve as a basis for all ionic measurements. If the reference signal is not steady and constant, the resulting ionic measurement will be inaccurate.

In the prior art, accuracy of the reference signal is ensured by routine maintenance of the meter. However, if field tests show a consistently inaccurate probe, a prior art pH meter is typically removed from service and shipped to a service facility for testing and calibration. Taking a meter out of service and returning it to a service facility is inconvenient. In addition, a replacement meter may need to be obtained for the duration. Further, the calibration process is costly.

Advantageously, the ionic probe 804 according to the invention includes at least two reference electrodes and generates at least two reference signals. The at least two reference signals can be used to perform self-correction of the probe (see FIG. 13 and the accompanying discussion).

Figure 9:
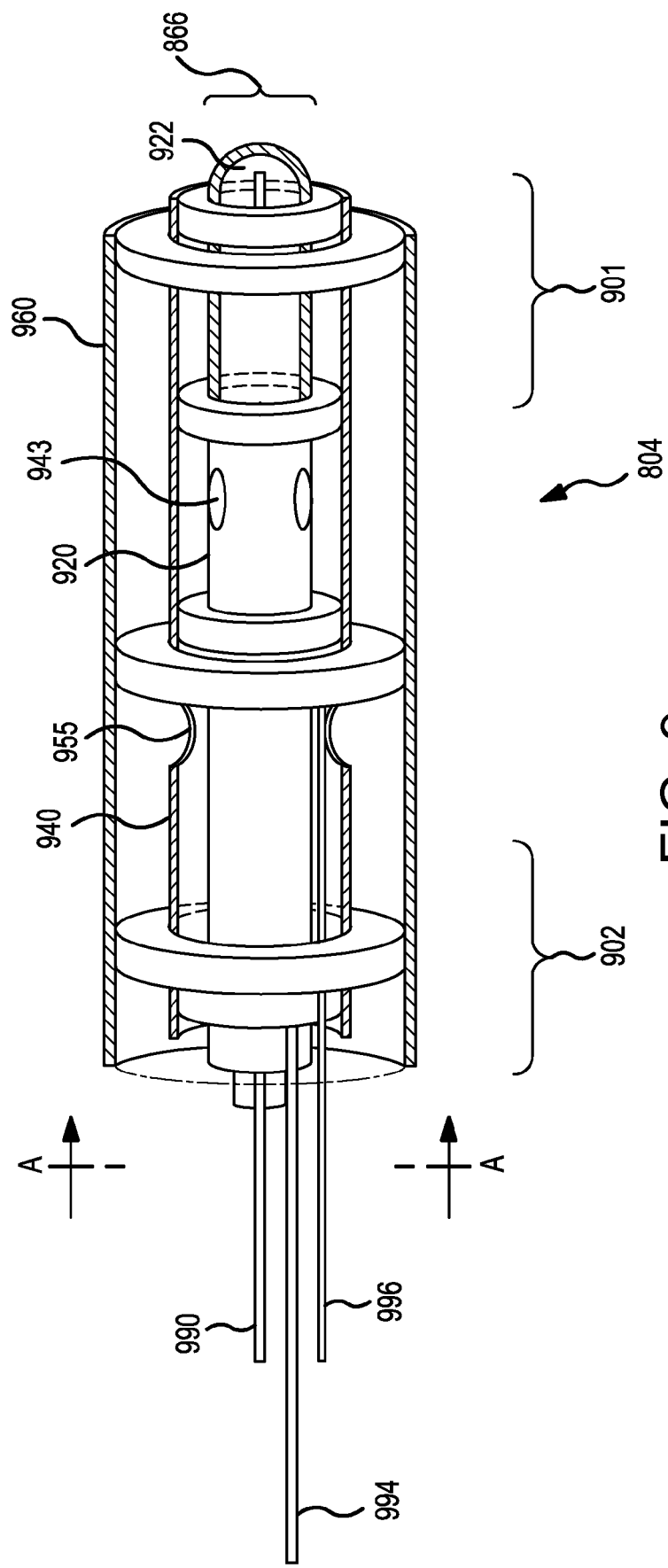
FIG. 9 shows the ionic probe according to an embodiment of the invention.

FIG. 9 shows the ionic probe 804 according to an embodiment of the invention. The ionic probe 804 includes a proximal end 901 and a distal end 902. The active ion sensitive region 866 is located at the proximal end 901 of the ionic probe 804. The ionic probe 804 includes an inner shell 920, a middle shell 940, and an outer shell 960. The shells 920, 940, and 960 in some embodiments are substantially coaxial. The shells 920, 940, and 960 in some embodiments are substantially mono-axial. The ionic probe 804 includes an active electrode 990, a first reference electrode 994, and a second reference electrode 996. The electrodes 990, 994, and 996 extend from the distal end 902 of the ionic probe 804 and may connect or attach to the cable 805. Alternatively, the electrodes 990, 994, and 996 can connect to some manner of internal circuit board or other component that is in turn connected to the cable 805 (see FIG. 12).

The electrodes 990, 994, and 996 can be formed of any suitable material. In some embodiments, the electrodes 990, 994, and 996 can be formed of silver/silver chloride, as is known in the art. However, other materials are contemplated and are within the scope of the description and claims.

The outer shell 960, and therefore the ionic probe 804 as a whole, can comprise a substantially cylindrical shape, as shown. However, it should be understood that the outer shell 960 and the ionic probe 804 can comprise any desired shape, including oval, rectangular, or even irregular in cross-section, for example.

The shells 960, 940, and 920 can comprise any suitable materials. For example, in one embodiment the outer shell 960 and the inner shell 920 comprise glass and the middle shell 940 comprises a metal shell, such as a stainless steel shell, for example. Consequently, the middle shell 940 can comprise a ground structure inside the ionic probe 804. However, other materials are contemplated and are within the scope of the description and claims.

The active ion sensitive region 866 extends from the first end of the ionic probe 804 and is designed to contact the external test fluid. The active electrode 990 resides in an active chamber 922 formed by the inner shell 920 and the active ion sensitive region 866. It should be understood that some or all of the ionic probe 804 may be immersed in the external test fluid, as previously noted.

The active ion sensitive region 866 allows ion interaction and therefore an ionic communication between an external test fluid and the active electrode 990. A millivolt potential is created across the interface between the active ion sensitive region 866 and the external aqueous solution (i.e., the external test fluid). The magnitude of this potential is dependent on the ionic value of the solution, such as the pH value, for example. The same is true of the ion sensitive region(s) 955 and the ion sensitive region(s) 943.

The ion sensitive regions 866, 943, and 955 can comprise any manner of ion reactive material that does not permit a fluid exchange between the inside and the outside of the outer shell 960, the middle shell 940, and the inner shell 920, respectively. For example, the active ion sensitive region 866 can be formed of an ion sensitive glass. The ion sensitive regions 866, 943, and 955 can comprise a specially formulated pH sensitive lithium ion-conductive glass comprising the oxides of silica, lithium, calcium, and other elements, for example. The structure of the pH glass allows lithium ion electrons to be exchanged by hydrogen ions in aqueous solutions, forming a hydrated layer on the exterior of the glass. However, other ion sensitive materials are contemplated and are within the scope of the description and claims.

The ion sensitive regions 866, 943, and 955 can comprise portions of the inner shell 920 and the middle shell 940. The ion sensitive regions 866, 943, and 955 can be molded or bonded into apertures in the inner shell 920 and the middle shell 940, for example. Alternatively, the ion sensitive regions 866, 943, and 955 can be formed in the inner shell 920 and the middle shell 940 during their formation.

Figure 10:
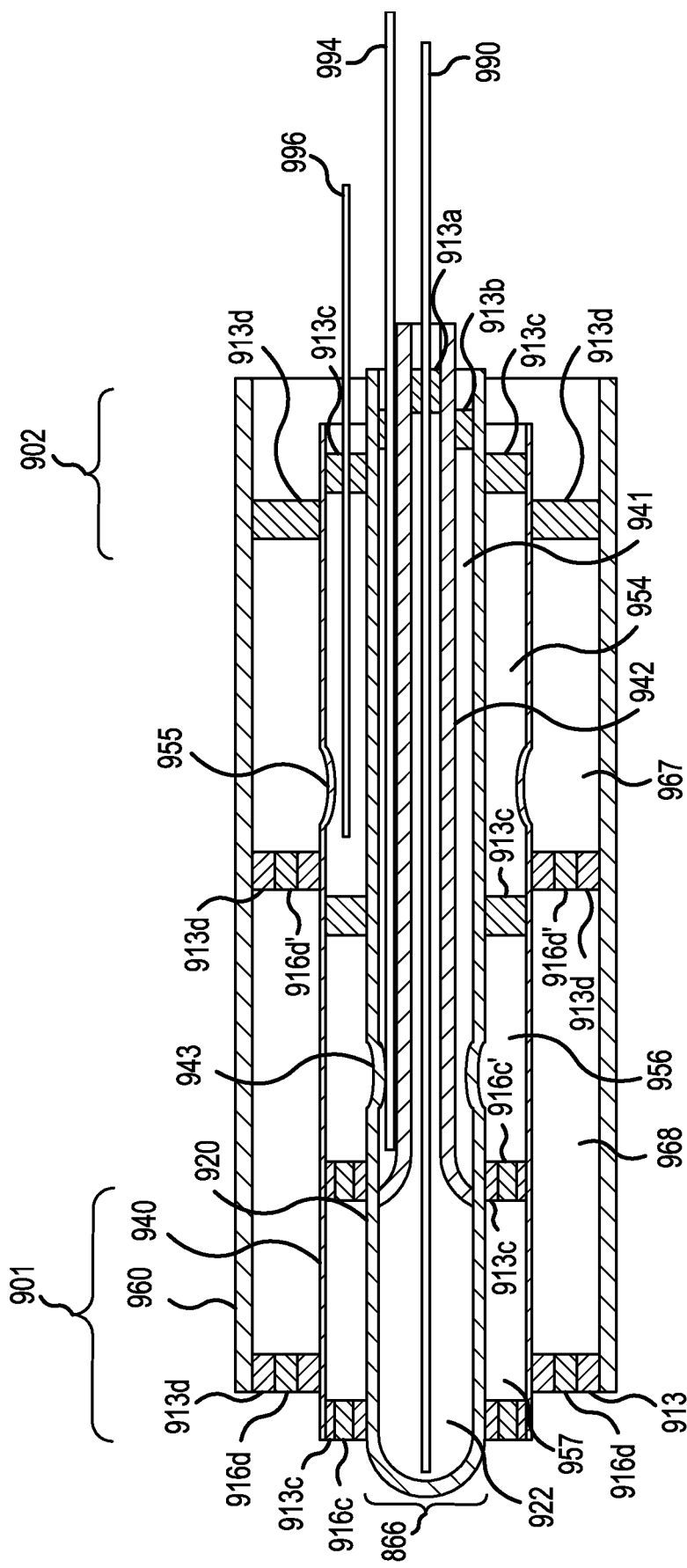
FIG. 10 is a longitudinal cross-section AA of the ionic probe according to an embodiment of the invention.

FIG. 10 is a longitudinal cross-section AA of the ionic probe 804 according to an embodiment of the invention. The cross-section is provided to clearly show the internal components of the ionic probe 804.

The inner shell 920 includes the active ion sensitive region 866, the active electrode 990, and an active electrolyte solution in the active chamber 922. The inner shell 920 further includes a ring seal 913a. The ring seal 913a seals the active electrolyte solution in the active chamber 922. The active electrode 990 can comprise any manner of electrode including a silver/silver chloride electrode. In operation, ions are exchanged at the hydrated exterior surface of the glass of the active ion sensitive region 866 in order to create a voltage potential inside the inner shell 920 and on the active electrode 990. Therefore, the active electrode 990 can be used to detect and measure this voltage potential, and the voltage potential is related to an ionic or pH value of the external test fluid, by comparison with one or more reference electrodes.

The inner shell 920 can include a middle divider 942 that forms a first reference chamber 941 within the inner shell 920. The first reference chamber 941 is substantially coaxial and/or mono-axial with the inner shell 920. Within the first reference chamber 941 is a first reference electrode 994 that is sealed within the chamber by a ring seal 913b. The first reference chamber 941 includes one or more first ion sensitive regions 943. The one or more first ion sensitive regions 943 allow an ion interaction between the first reference solution in the first reference chamber 941 and a middle solution that is external to the inner shell 920, such as in a middle reference solution chamber 956. The middle solution can be maintained at a substantially constant pH value. The pH values of the first reference solution and the middle solution determine the voltage potential across the one or more first ion sensitive regions 943. A voltage potential between the first reference electrode 994 and the active electrode 990 can be detected and measured, wherein the reference voltage potential may be used for self-correction, as will be discussed later.

One or more ring seals 913c seal the inner shell 920 inside the middle shell 940. One or more of the ring seals 913c can include one or more ceramic pins or frits 916c. The ceramic pins 916c allow ion exchange between adjacent compartments formed by ring seals 913c.

In one portion of the middle shell 940, consecutive ring seals 913 form a second reference chamber 954. The second reference chamber 954 is substantially annular and is located between the inner shell 920 and the outer shell 940. The second reference electrode 996 is positioned in this second reference chamber 954. The second reference chamber 954 further includes one or more second ion sensitive regions 955. The one or more second ion sensitive regions 955 allow ion interaction between a second reference solution within the second reference chamber 954 and a first outer reference solution in a first outer reference chamber 967 located between the middle shell 940 and the outer shell 960. As discussed above, the voltage potential across the one or more second ion sensitive regions 955 is determined by the pH value of the second reference solution and the pH value of the first outer reference solution.

The first outer reference chamber 967 can be substantially annular. The volume between the outer shell 960 and the middle shell 940 can be divided into multiple chambers by ring seals 913d and/or ring seals 913d plus ceramic pins 916d. For example, in the embodiment shown the ionic probe 804 includes two such chambers 967 and 968. The first outer reference chamber 967 contains a first outer reference solution or gel (such as a first salt gel) and the second outer reference chamber 968 contains a second outer reference/fill solution or gel (such as a second salt gel).

A salt (or ionic) bridge comprises a reference solution between ionic junctions, wherein the reference solution and the junctions enable ion transfer and exchange with the external test fluid. In a salt bridge, the reference solutions comprise salt solutions or salt gels, but other ionic solutions or gels can be employed. One salt bridge in the figure comprises the ceramic pin 916*d*, the second reference solution in the second outer reference chamber 968, the ceramic pin 916*d'*, and the first reference solution in the first outer reference chamber 967. Another salt (or ionic) bridge in the figure comprises the ceramic pin 916*c*, a reference solution in the third middle reference chamber 957, the ceramic pin 916*c'*, and a middle solution in the second middle reference chamber 956.

A ceramic pin or frit 916 interfaces to a contacting liquid or gel. A ceramic pin 916 comprises an ionic junction that allows ion exchange and therefore an ionic communication between fluids on both sides. The ceramic pin 916 can comprise any matter of ion transmissive material that does not enable a fluid exchange. However, other materials are contemplated and are within the scope of this description and claims.

As a result of the third middle reference chamber 957 and the second middle reference chamber 956, the first ion sensitive region 943 is in ionic communication with the external test fluid. However, the first reference electrode 994 is encased in a glass chamber formed of part of the inner shell 920 and the middle divider 942.

As a result of the second outer reference chamber 968 and the first outer reference chamber 967, the second ion sensitive region 955 is in ionic communication with the external test fluid. However, the second reference electrode 996 is encased in a glass chamber formed of part of the inner shell 920 and part of the middle shell 940.

The two resulting glass chambers hold reference/fill solutions in contact with the corresponding reference electrodes 944 and 996. The corresponding ion sensitive regions 943 and 955 allow ionic interaction with the two internal reference solutions and therefore with the two intermediate solutions within the chambers 957 and 968. A voltage potential is consequently generated across the glass wall and is detected via the internal reference electrodes in their respective electrolyte solutions. The reference solution in each reference chamber dictates the voltage potential in the hydrated layer at the outside of the respective ion sensitive region 955 or 943.

The major problem with combination pH probes having a reference electrode in a reference chamber is in the junction between the internal reference solution and the external fluid. The junction is vital to the function of the reference electrode and to the establishment of an ionic circuit. Clogging or failure of the junction usually leads to very slow and/or erroneous readings. The junction can also allow the contamination of the internal reference solution by the external test fluid. This poisons a prior art reference electrode, rendering a prior art pH probe inaccurate. As a result, the prior art reference electrode commonly has to be replaced after a duration of use. Some manufacturers have attempted to overcome this problem by the employment of multiple junctions and chambers between the prior art reference electrode and the exterior medium. Others have used flowing junctions in which a continuous supply of reference solution is fed to the prior art reference electrode compartment and exits via a small hole or ground glass aperture. This prevents the contamination of the reference solution and the prior art reference electrode. However, it has the disadvantage of requiring additional expensive and complex apparatus for conducting and metering the solution into the prior art reference electrode chamber.

However, the problem is overcome by encasing a reference electrode in a substantially ion-impermeable chamber, such as a glass chamber as shown in the construction of U.S. Pat. No. 6,395,158 to King et al., for use in differential pH probes. The reference electrode is immersed in a reference solution held in the impermeable chamber and communicates with the external test fluid via salt (or other ionic) bridges and an ion sensitive region forming part of the impermeable chamber. A salt bridge comprises reference solutions or gels and ceramic pins, as previously discussed. The salt bridges can comprise replaceable ceramic pins and replaceable liquids/gels. Provision is made to change both the ceramic pins and the solutions during routine maintenance procedures, such as where the solutions in the chambers 956 and 957 and in the chambers 967 and 968 have become contaminated.

Because each reference electrode 994 and 996 is encapsulated in a glass chamber, there is less likelihood of poisoning. Since the internal reference solution for each of the reference electrodes 994 and 996 is buffered, its pH value is kept constant. As a result, the measured potential difference is dependent only upon the ionic or pH value of the external test fluid being measured. As a result, the voltage potentials on the reference electrodes 994 and 996 remain essentially constant over time, regardless of the ionic level or content of the external test fluid, while completing a circuit between the reference electrodes 994 and 996 and the active electrode 990. Consequently, an active voltage potential at the active electrode 990 can be compared to one or more resulting reference values in order to determine a pH level or other ionic level. In addition, the reference signals can be compared to other standards in order to calibrate the ion meter 800.

Where the ionic probe 804 includes two reference electrodes 994 and 996, the corresponding glass chambers 941 and 954 can hold solutions of different pH values or of different ionic characteristics. For example, the first reference solution can comprise a 4.0 pH solution and the second reference solution can comprise a 7.0 pH solution. It should be understood that any desired pH values can be used, and the above numbers are given for illustration only.

The two reference electrodes 994 and 996 can be used to self-calibrate the ionic probe 804. As previously discussed, the two reference electrodes 994 and 996 can be used to self-calibrate a meter employing the ionic probe 804, such as a pH meter, for example.

The active solution in the active electrode chamber 922 can comprise any suitable solution that can exchange ions with the active ion sensitive region 866. The reference solutions for each of the reference electrodes 994 and 996 can comprise any suitable solution that can exchange ions with the ion sensitive regions 943 and 955.

Figure 11:
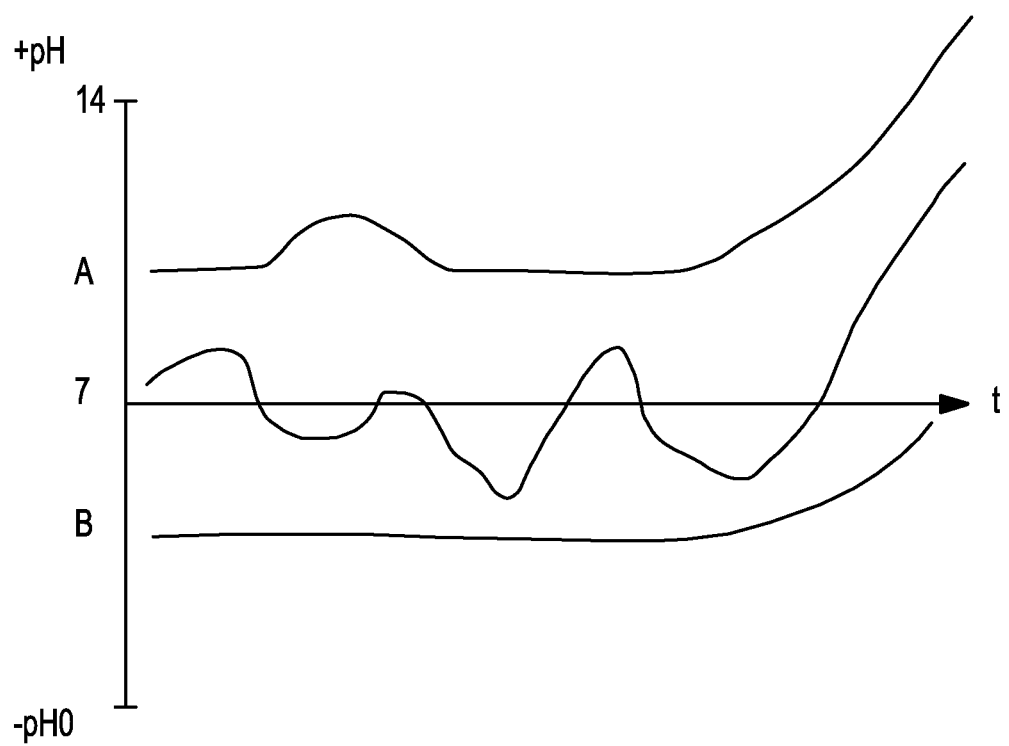
FIG. 11 is a graph representing first and second reference signals according to an embodiment of the invention.

FIG. 11 is a graph representing first and second reference signals according to an embodiment of the invention. The graph shows a reference signal A and a reference signal B. The erratic line between the two reference signals A and B represents a measurement signal over a long period of time. It should be understood that for a single test fluid, the measurement signal should be relatively constant and an erratic signal is shown for clarity.

It can be seen from the figure that a measurement value can be obtained from a comparison of the measurement signal to one or both of the reference signals A and B. For example, where the reference signal A is generated for a reference solution of a first pH value and where the reference signal B is generated for a reference solution of a second pH value, then the measurement signal can be compared to the reference signals and the measurement value can be determined according to a predetermined algorithm. The algorithm can perform any manner of correlation, extrapolation, interpolation, etc.

It should be understood that only one reference signal is required in order to obtain the measurement signal. However, it should be apparent that the ionic measurement value determination will be easier and will be more accurate in the presence of at least two reference signals. More than two reference signals can be employed, if desired.

A further advantage is that two or more reference signals allow and enable the ion meter 800 to be self-calibrating and/or self-compensating. The graph shows a first deviation or bump in the reference signal A. The bump can be caused by various factors, such as temperature changes, clogging of a salt bridge, etc. By comparing the reference signal A and the reference signal B, the bump can be detected and ignored, minimizing or eliminating errors. Consequently, one reference signal can be used to check on the other reference signal (s). The comparison can therefore be used to detect a single reference drift in one of the reference signals.

If both reference signals are diverging from an essentially steady state, then this error condition can also be detected. If both (or two or more) reference signals are diverging in a roughly parallel manner, then they may be indicating some manner of poisoning or contamination of the reference solutions. The comparison can therefore be used to detect a dual reference drift in two reference signals. If the divergence is not excessive, then a computational factor can be derived that can be used to correct the reference signals.

In some embodiments, the two or more reference signals can be compared to a predetermined constant, such as a predetermined voltage level. The predetermined constant can be used to determine when the two or more reference signals are diverging from a predetermined expected value.

Figure 12:
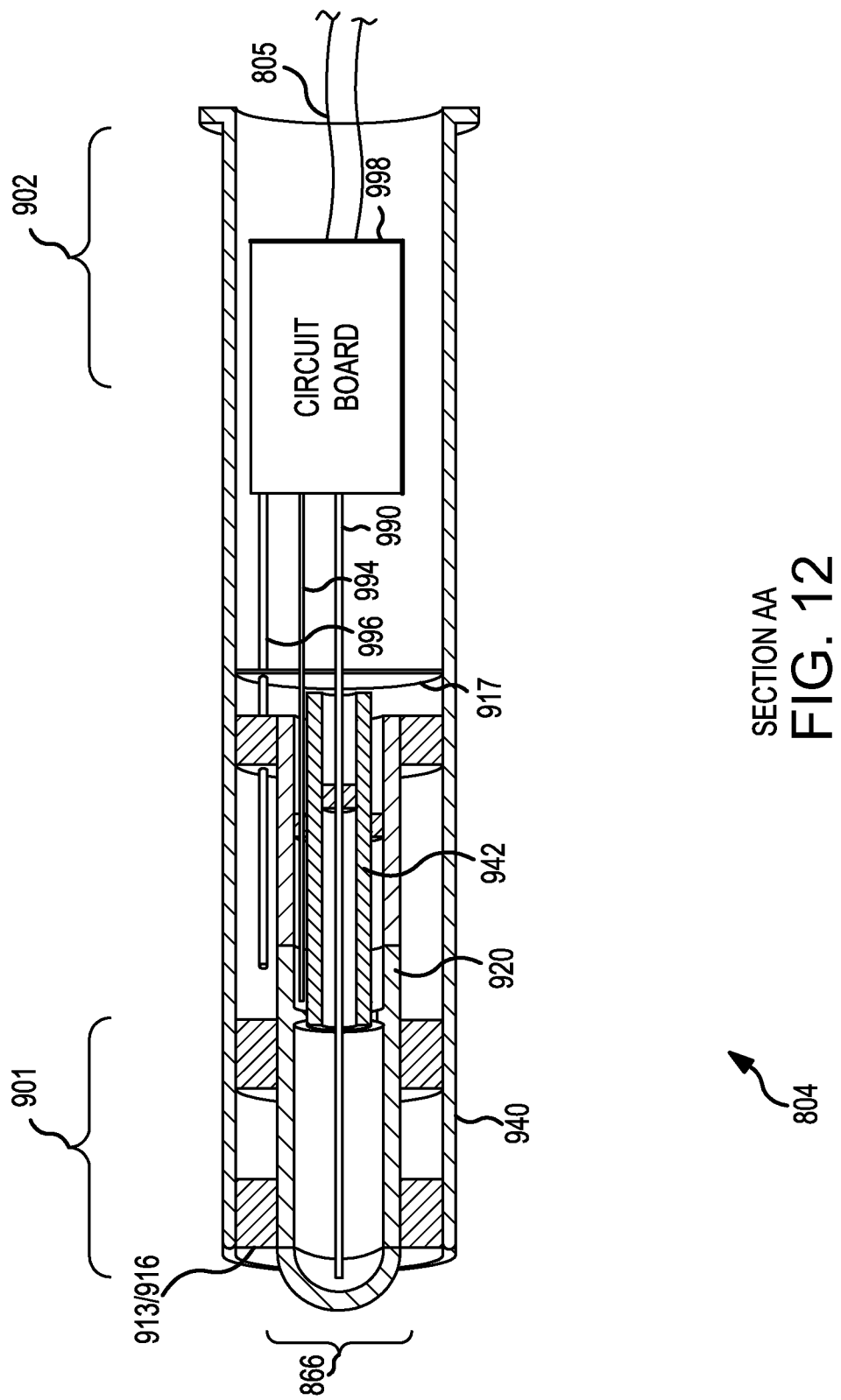
FIG. 12 is a longitudinal cross-section AA of the ionic probe according to an embodiment of the invention.

FIG. 12 is a longitudinal cross-section AA of the ionic probe 804 according to an embodiment of the invention. In addition to the previously recited components, the ionic probe 804 can include a bulkhead 917 that seals off a portion of the proximal end 901. A circuit board 998 can be located in the distal end 902. A seal or end portion can substantially seal the circuit board 998 in the ionic probe 804. The circuit board 998 can be connected to the electrodes 990, 994, and 996, and can be further connected to the cable 805.

The circuit board 998 can perform any manner of amplification, buffering, and/or processing, as needed.

Figure 13:
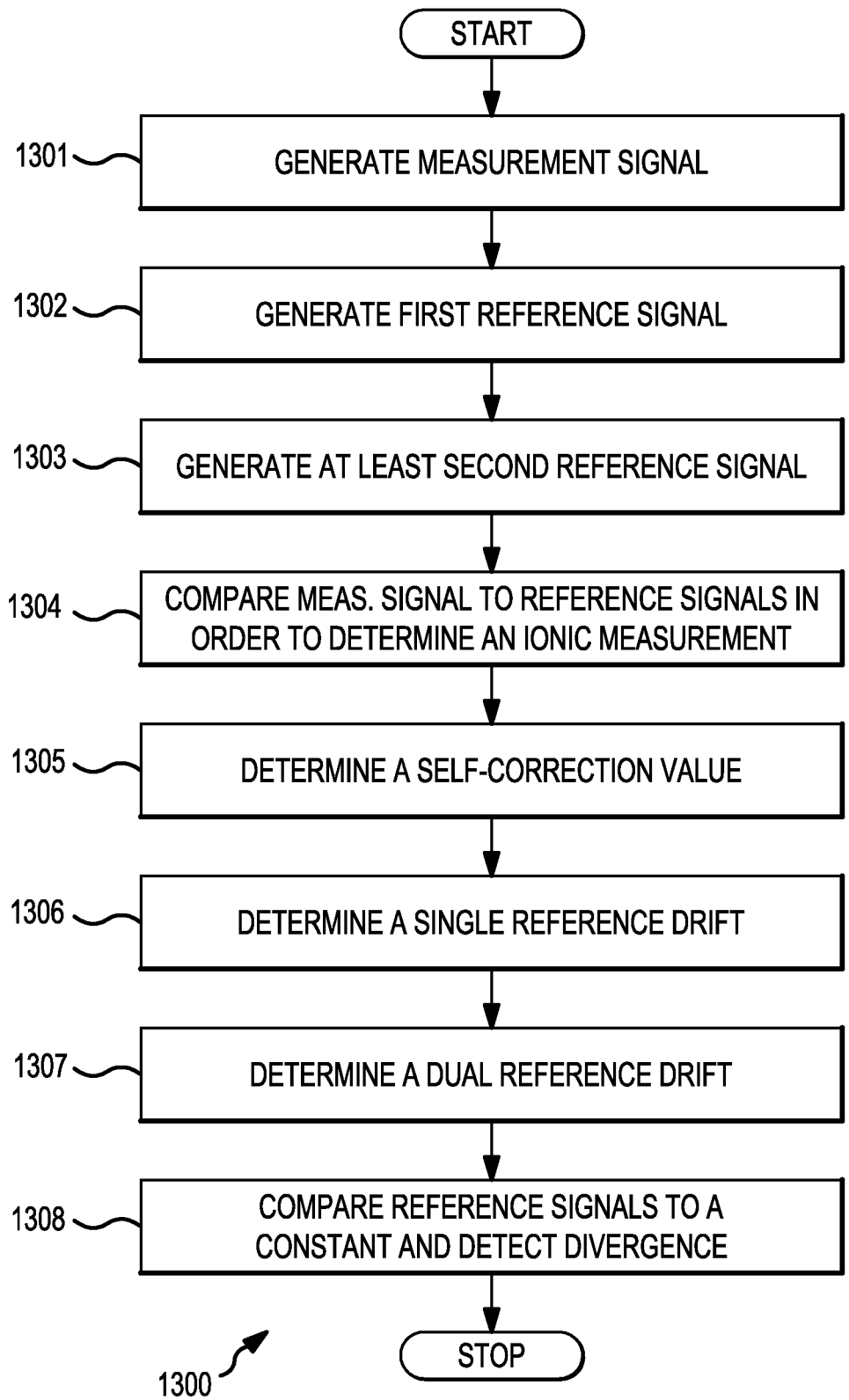
FIG. 13 is a flowchart of a self-correction method for an ionic meter according to an embodiment of the invention.

FIG. 13 is a flowchart 1300 of a self-correction method for an ionic meter according to an embodiment of the invention. The method enables an ionic meter and corresponding ionic probe to perform a self-correction, such as self-calibration and/or self-compensation processes. A self-calibration or self-compensation process can detect an error, inconsistency, or change in the readings produced by the ionic meter and can add or subtract a correction amount in order to ensure the accuracy and consistency of an ionic measurement. In step 1301, an ionic meter generates a measurement signal. The measurement signal comprises a measurement related to the ionic characteristic of an external test fluid. In some embodiments, the measurement signal comprises a voltage signal, but it should be understood that other signals can be employed.

In step 1302, a first reference signal is generated. The first reference signal can be generated by a first reference electrode and/or a first reference electrode assembly.

In step 1303, a second reference signal is generated. The second reference signal can be generated by a second reference electrode and/or a second reference electrode assembly.

In step 1304, the measurement signal is compared to the first and second reference signals in order to determine an ionic measurement. As a result, given that the first and second reference signals are substantially known ionic values, the ionic measurement can be determined from the measurement signal. The comparison can result in a correlation, extrapolation, or interpolation of the resulting ionic measurement from the initial measurement signal. The comparison can result in a lookup table, formula completion, or other algorithmic solution for the ionic measurement. For example, wherein the first reference signal comprises a relatively low pH value and the second reference signal comprises a relatively high pH value, the ionic measurement can be determined from a relative distance of the ionic measurement signal to the two reference signals.

In step 1305, a correction value can be determined from the comparison. The correction value can comprise a value to be added to or subtracted from an ionic measurement value. For example, after a correlation, extrapolation, or interpolation of the ionic measurement, a correction value can be determined and used to refine the ionic measurement value.

In step 1306, a single reference drift amount can be determined from the comparison. For example, one of the reference signals can be compared to the other signal and/or to stored historical values. Any deviation by the reference signal under comparison can be noted and flagged. Any deviation by the reference signal under comparison can be corrected by a non-affected reference signal. For example, if one reference signal goes up or down in value, it can be corrected to maintain a predetermined difference from the other reference signal.

In step 1307, a dual reference drift amount can be determined from the comparison. For example, both reference signals can be compared to stored historical values and any significant deviation can be noted and compensated for.

In step 1308, the first and second reference signals can be compared to a predetermined constant, such as a constant voltage level. Any divergence by one or both of the reference signals can be determined. As before, a diverging reference signal can be corrected by using the predetermined constant.

The ionic probe according to some embodiments can provide a probe that uses two reference electrodes, providing a self-correction capability. The two reference electrodes are glass-encased, eliminating electrolyte contamination, and thus a longer life, a lower operating cost, and requiring less maintenance.

We claim:

1. An ionic probe, comprising:
    an inner shell, an outer shell, and a middle shell configured to house one or more electrodes, wherein an outer surface of the inner shell is contiguous material that includes a first pH-sensitive material and a second pH-sensitive material;
    wherein the inner shell is disposed within the middle shell and the middle shell is disposed within the outer shell;
    an active electrode disposed in the inner shell that generates a measurement signal for an external test fluid;
    a first reference electrode disposed in the inner shell in a first reference chamber formed by an inner divider in the inner shell, the first reference electrode generating a first reference signal;
    a second reference electrode disposed in a second reference chamber formed by the inner shell and the middle shell, the second reference chamber generating a second reference signal;
    wherein the measurement signal is provided by the ionic probe for comparison to the first reference signal and the second reference signal in order to determine an ionic measurement of the external test fluid.

2. The ionic probe of claim 1, with the active electrode being located in an active electrolyte that ionically interacts with the external test fluid, with the first reference electrode being located in a first reference solution that ionically interacts with a middle solution, and with the second reference electrode being located in a second reference solution that ionically interacts with an outer solution, wherein the middle solution and the second reference solution ionically interact with the external test fluid.

3. The ionic probe of claim 1, wherein the inner shell forms an active chamber and including an active electrolyte solution and an active ion sensitive region that protrudes from the ionic probe and is adapted to contact the external test fluid, with the active ion sensitive region allowing ion interaction between the active electrolyte solution and the external test fluid;
the active electrode located in the active chamber and configured to generate a measurement signal related to an ionic potential between the external test fluid and the active electrolyte solution;
the first reference chamber holding a first reference solution and including at least one first ion sensitive region formed in the inner shell, with the at least one first ion sensitive region allowing ion interaction between the first reference solution and a middle solution that is external to the inner shell at the first ion sensitive region;
the first reference electrode located within the first reference chamber and configured to generate a first reference signal related to an ionic potential between the first reference solution and the middle solution;
the middle shell forming a second reference chamber and holding a second reference solution and including at least one second ion sensitive region formed in the middle shell, with the at least one second ion sensitive region completing a circuit between the second reference solution and an outer solution that is external to the middle shell at the second ion sensitive region; and
the second reference electrode being located in the second reference chamber and configured to generate a second reference signal related to an ionic potential between the second reference solution and the outer solution.

4. The ionic probe of claim 3, wherein one or more of the active ion sensitive region, the at least one first ion sensitive region, or the at least one second ion sensitive region comprise patches of ion sensitive material bonded to the inner shell and the middle shell.

5. The ionic probe of claim 3, where the inner shell, the inner divider, and the middle shell are substantially mono-axial/coaxial.

6. The ionic probe of claim 3, wherein the outer shell holds at least an outer solution, with the outer solution being configured to ionically interact with the second reference solution through the at least second ion sensitive region.

7. The ionic probe of claim 3, wherein the outer shell, the inner shell, the middle shell, and the inner divider are substantially mono-axial/coaxial.

8. The ionic probe of claim 1, wherein the first reference signal is compared to the second reference signal in order to determine a correction value to be applied to the ionic measurement.

9. The ionic probe of claim 1, wherein the first reference signal is compared to the second reference signal in order to detect a single reference drift in one of the first reference signal or the second reference signal.

10. The ionic probe of claim 1, wherein the first reference signal and the second reference signal are compared to a predetermined reference voltage in order to detect a dual reference drift in both the first reference signal and the second reference signal.

11. An ionic probe, comprising:
an inner shell, an outer shell, and a middle shell, wherein the inner shell the middle shell house one or more electrodes and at least one of the inner shell and the middle shell has an outer surface that is contiguous material that includes a first pH-sensitive material and a second pH-sensitive material;
wherein the inner shell is disposed within the middle shell and the middle shell is disposed within the outer shell;
the inner shell forming an active chamber and including an active electrolyte solution and an active ion sensitive region that protrudes from the ionic probe and is adapted to contact an external test fluid, with the active ion sensitive region allowing ion interaction between the active electrolyte solution and the external test fluid;
an active electrode located in the active chamber and configured to generate a measurement signal related to an ionic potential between the external test fluid and the active electrolyte solution;
a middle divider located inside the inner shell and forming a first reference chamber, with the first reference chamber holding a first reference solution and including at least one first ion sensitive region formed in the inner shell, with the at least one first ion sensitive region allowing ion interaction between the first reference solution and a middle solution that is external to the inner shell at the first ion sensitive region;
a first reference electrode located within the first reference chamber that generates a first reference signal related to an ionic potential between the first reference solution and the middle solution;
the middle shell and the inner shell forming a second reference chamber and holding a second reference solution and including at least one second ion sensitive region formed in the middle shell, with the at least one second ion sensitive region allowing ion interaction between the second reference solution and an outer solution that is external to the middle shell at the second ion sensitive region;
a second reference electrode located in the second reference chamber that generates a second reference signal related to an ionic potential between the second reference solution and the outer solution;
wherein the measurement signal is provided by comparison to the first reference signal and the second reference signal in order to determine an ionic measurement of the external test fluid.

12. The ionic probe of claim 11, wherein one or more of the active ion sensitive region, the at least one first ion sensitive region, or the at least one second ion sensitive region comprise patches of ion sensitive material bonded to the inner shell and the middle shell.

13. The ionic probe of claim 11, wherein the first reference signal is compared to the at least second reference signal in order to determine a correction value to be applied to the ionic measurement.

14. The ionic probe of claim 11, wherein the first reference signal is compared to the at least second reference signal in order to detect a single reference drift in one of the first reference signal or the at least second reference signal.

15. The ionic probe of claim 11, wherein the first reference signal and the at least second reference signal are compared to a predetermined reference voltage in order to detect a dual reference drift in both the first reference signal and the at least second reference signal.

16. The ionic probe of claim 11, where the inner shell, the middle shell, and the outer shell are substantially mono-axial/coaxial.

17. The ionic probe of claim 11, wherein the outer shell holds at least an outer solution, with the outer solution being configured to ionically interact with the second reference solution through the at least second ion sensitive region.

18. The ionic probe of claim 11, wherein the outer shell, the inner shell, the middle shell, and the inner divider, are substantially mono-axial/coaxial.

19. An ionic meter, comprising:
an ionic probe comprising:
at least an outer shell, an inner shell and a middle shell configured to house one or more electrodes, wherein an outer surface of the inner shell is contiguous material that includes a first pH-sensitive material and a second pH-sensitive material;
wherein the inner shell is disposed within the middle shell and the middle shell is disposed within the outer shell;
an active electrode disposed in the inner shell that generates a measurement signal for an external test fluid;
a first reference electrode disposed in the inner shell in a first reference chamber formed by an inner divider in the inner shell, the first reference electrode generating a first reference signal; and
a second reference electrode disposed within a second reference chamber formed by the inner shell and the middle shell, the second reference electrode generating a second reference signal; and
a processor configured to receive the measurement signal, the first reference signal and the second reference signal and compare the measurement signal to the first reference signal and the second reference signal in order to determine an ionic measurement of the external test fluid.

20. The ionic meter of claim 19, with the active electrode being located in an active electrolyte that ionically interacts with the external test fluid, with the first reference electrode being located in a first reference solution that ionically interacts with a middle solution, and with the second reference electrode being located in a second reference solution that ionically interacts with an outer solution, wherein the middle solution and the outer solution ionically interact with the external test fluid.

21. The ionic meter of claim 19, with the processor being further configured to compare the first reference signal to the second reference signal in order to determine a correction value to be applied to the ionic measurement.

22. The ionic meter of claim 19, with the processor being further configured to compare the first reference signal to the second reference signal in order to detect a single reference drift in one of the first reference signal or the second reference signal.

23. The ionic meter of claim 19, with the processor being further configured compare the first reference signal and the second reference signal to a predetermined reference voltage in order to detect a dual reference drift in both the first reference signal and the second reference signal.

24. The meter of claim 19, where the inner shell, the middle shell, and the outer shell are substantially mono-axial/coaxial.

25. The meter of claim 20, wherein the outer shell holds at least an outer solution, with the outer solution being configured to ionically interact with the second reference solution through the at least second ion sensitive region.

26. The meter of claim 19, wherein the outer shell, the inner shell, the middle shell, and the inner divider are substantially mono-axial/coaxial.

* * * * *